(12) United States Patent
Cross, III

(10) Patent No.: US 12,036,206 B2
(45) Date of Patent: *Jul. 16, 2024

(54) COMPOSITIONS AND METHODS FOR PAIN RELIEF

(71) Applicant: William H. Cross, III, Waco, TX (US)

(72) Inventor: William H. Cross, III, Waco, TX (US)

( * ) Notice: Subject to any disclaimer, the term of this patent is extended or adjusted under 35 U.S.C. 154(b) by 244 days.

This patent is subject to a terminal disclaimer.

(21) Appl. No.: 17/352,674

(22) Filed: Jun. 21, 2021

(65) Prior Publication Data

US 2021/0322374 A1  Oct. 21, 2021

Related U.S. Application Data

(63) Continuation of application No. 15/017,527, filed on Feb. 5, 2016, now Pat. No. 11,040,022.

(60) Provisional application No. 62/112,598, filed on Feb. 5, 2015.

(51) Int. Cl.
| | | |
|---|---|---|
| *A61K 31/385* | (2006.01) | |
| *A61K 31/185* | (2006.01) | |
| *A61K 31/197* | (2006.01) | |
| *A61K 31/198* | (2006.01) | |
| *A61K 31/225* | (2006.01) | |

(52) U.S. Cl.
CPC .......... *A61K 31/385* (2013.01); *A61K 31/185* (2013.01); *A61K 31/197* (2013.01); *A61K 31/198* (2013.01); *A61K 31/225* (2013.01)

(58) Field of Classification Search
CPC .... A23V 2250/0612; A23V 2250/0616; A23V 2250/0632; A23V 2250/0644; A61K 31/197–198
See application file for complete search history.

(56) References Cited

U.S. PATENT DOCUMENTS

| 3,711,602 | A | 1/1973 | Herschler | |
|---|---|---|---|---|
| 5,719,119 | A | 2/1998 | Veech | |
| 7,060,295 | B2 | 6/2006 | Richardson | |
| 7,645,742 | B2 | 1/2010 | Stohs | |
| 9,414,615 | B2 | 8/2016 | Sridhar | |
| 10,945,979 | B1 | 3/2021 | Schroeder | |
| 11,040,022 | B2 * | 6/2021 | Cross, III | A61K 31/197 |
| 2001/0011083 | A1 | 8/2001 | Barr | |
| 2001/0031744 | A1 | 10/2001 | Kosbab | |
| 2005/0129783 | A1 | 6/2005 | McCleary | |
| 2011/0064712 | A1 * | 3/2011 | Amato | A61K 31/295 562/571 |
| 2011/0313043 | A1 | 12/2011 | Kramer | |
| 2012/0232003 | A1 | 9/2012 | Takahashi | |
| 2014/0044685 | A1 | 2/2014 | Greenberg | |
| 2016/0228409 | A1 | 8/2016 | Cross, III | |
| 2017/0312329 | A1 | 11/2017 | Cross, III | |

FOREIGN PATENT DOCUMENTS

| CN | 101716182 | 4/2013 |
|---|---|---|
| IN | 1306CHE2007 | 1/2009 |
| WO | 2008048045 | 4/2008 |
| WO | 2013108262 | 7/2013 |

OTHER PUBLICATIONS

Dietary Reference Intakes for Thiamin, Riboflavin, Niacin, Vitamin B6, Folate, Vitamin B12, Pantothenic Acid, Biotin, and Choline. A Report of the Standing Committee on the Scientific Evaluation of Dietary Reference Intakes . . . Institute of Medicine, National Academy Press, Washington, DC 1998. (Year: 1998).*
Bell, D.S.H., 2012, Case Report in Endocrinology, Article ID 165056, 3pp.
Curtis, L., 2013, International Journal of Diabetes Research, 2:56-60.
Hagen, M. et al., 2017, Current Medical Research and Opinion, 33(9):1623-1634.
Henriksen, E.J., 2006, Free Radical Biology & Medicine, 40:3-12.
Lautt et al., 2010, Can. J. Physiol. Pharmacol., 88:313-323.
Shinohara, T. et al., 2004, J. Biol. Chem., 279:23559-23564.
Vita Sciences, Nervex Neuropathy Pain Relief (Product Literature), Jan. 26, 2017.
Wagner, T., 2012, Pain Management, 2(3):239-250.
Wojtczak, A., 2002, Medical Teacher, 24:658-660.
Yonguc, et al., 2015, Gene, 555:119-126.
McCarty, M.F., 2017, Healthare, 5, 28pp (doi:10.3390/healthcare5010015).
U.S. Appl. No. 15/017,527, 20160228409, Aug. 11, 2016.
U.S. Appl. No. 15/496,919, 20180303896, Oct. 25, 2018.
U.S. Appl. No. 15/650,825, 20170312329, Sep. 6, 2019.
U.S. Appl. No. 16/264,595, 20190231806, Aug. 1, 2019.
U.S. Appl. No. 16/264,609, 20190231807, Aug. 1, 2019.
U.S. Appl. No. 16/264,614, 20190231725, Aug. 1, 2019.
U.S. Appl. No. 16/283,660, 20190275154, Sep. 12, 2019.

* cited by examiner

*Primary Examiner* — Theodore R. Howell
(74) *Attorney, Agent, or Firm* — Thomas | Horstemeyer, LLP

(57) ABSTRACT

The invention provides pharmaceutical compositions having improved effects and synergistic efficacy against pain, and provides methods for their use to treat pain, wherein the composition comprises: a sulfur-containing amino acid; a carnitine compound; and at least one compound that is a L-citrulline compound or a beta-alanine compound.

23 Claims, No Drawings

COMPOSITIONS AND METHODS FOR PAIN RELIEF

RELATED APPLICATIONS

This application claims priority upon U.S. nonprovisional application Ser. No. 15/017,527 filed on Feb. 5, 2016, which claims priority upon provisional U.S. patent application Ser. No. 62/112,598, filed Feb. 5, 2015, the contents of which are incorporated by reference herein in their entireties.

FIELD OF THE INVENTION

The invention concerns compositions and methods for the treatment of pain.

BACKGROUND

Chronic pain is a ubiquitous global problem, though estimates of its incidence vary depending on how the term "chronic" is defined as to pain frequency, intensity and duration. The World Health Organization estimates that 22% of primary care patients have chronic debilitating pain. And chronic pain has been estimated to affect 28% to 65% of U.S. adults. Neuropathic pain has been particularly difficult to diagnose and mitigate. Chronic pain is estimated to be severe for 5% of the population. See Barbara P. Yawn et al., "The prevalence of neuropathic pain: Clinical evaluation compared with screening tools in a community population," Pain Med., 10 (3): 586-593 (April 2009).

Neuropathy is an abnormal, usually degenerative systemic condition of the nerves or nervous system. Typical symptoms include weakness, numbness and pain, and these may occur in stark episodes. Neuropathic pain may be in the form of dysesthesia (abnormal sensations) or allodynia (stimuli that are painful in the context, but otherwise normally non-painful). The pain may be continuous and/or paroxysmal (episodic). Paroxysmal pain has a stabbing or electric shock type of characteristic. Other common variations include feelings of burning or coldness, stabbing tingling, numbness and itching. By contrast, nociceptive pain is usually an aching. Neuropathic pain is typically classified as being associated with the peripheral nervous system, the central nervous system (brain and spinal cord), or some mixture of those.

The prevalence of neuropathic pain is demonstrated by the conditions with which it appears. Severe peripheral neuropathic pain occurs commonly in diabetes and other metabolic disorders, herpes zoster infection, HIV-related neuropathies, malnutrition, toxins, remote manifestations of malignancies, immune-mediated disorders and physical trauma to a nerve trunk. Central neuropathic pain arises in spinal cord injuries, multiple sclerosis, and some strokes. Neuropathic pain is also common in cancer, where it arises from surgery, radiation injury, chemotherapy-induced peripheral neuropathy, and by tumors that compress peripheral nerves.

Many neuropathies are diagnosed according to the nerve centers that they affect; variations affect the peripheral nervous system, cranial nerves, auditory nerve, optic nerve (including "Leber's hereditary optic neuropathy"), organization of neurofilaments (giant axonal neuropathy), and autonomic [and sometimes also sensory or motor] nerves (autosomal dominant familial amyloid neuropathies). Other neuropathies are diagnosed according to their cause or other activity, such as diabetic neuropathy, hereditary neuropathy with liability to pressure palsy (HNPP, affecting sensory and muscle nerves), neuropathy target esterase (enzymatic rate increases), "neuropathy, ataxia, and retinitis pigmentosa" (NARP, with various manifestations), delayed neuropathy induced by organophosphate poisoning, and polyneuropathy (accompanied by malfunction of many peripheral nerves simultaneously). Neuropathy is not to be confused with other disorders of the nervous system, such as encephalopathy, myelopathy, radiculopathy, neuromuscular junction disease and myopathy.

Neuropathy has several sources, depending on the particular variation, The source of peripheral nerve pain is often aberrant regeneration after formation of a lesion there; the neurons then become hyper-sensitized to chemical, thermal and mechanical stimuli. By contrast, central nerve pain arises from the spinothalamic tract (STT, from the spinal cord dorsal horn neurons) representing the major ascending nociceptive pathway. Due to ongoing spontaneous activity in the peripheral system, STT neurons become hyper-sensitized and have higher background activity (electrical noise), larger receptive fields and greater responses to afferent impulses. Thus normally mild tactile stimuli seem painful and persistent.

STT neurons may also be affected in other ways. Central neural hypersensitization may follow peripheral nerve damage; the loss of afferent signals induces functional changes in dorsal horn neurons. Moreover a drop in input of large fiber lowers interneuron activity inhibiting nociceptive neurons, that is, afferent inhibition is lost. Reduced activity of the descending antinociceptive systems or loss of descending inhibition may also contribute. As input from the neuron is lost (i.e, deafferentation occurs) the STT neurons begin to fire spontaneously (also called "deafferentation hypersensitivity.").

Those are not the only mechanisms. In another mechanism, glial cells (i.e., neuroglia) are induced by peripheral nerves to release proinflammatory cytokines and glutamate, contributing to the effect on central neurons. In yet another mechanism, gene expression is altered as is expression of ion channels, causing changes in neurotransmitters and response to neural input.

Many methods have been used to treat neuropathic pain, but with limited benefit. It is difficult to treat, and usually only 40% to 60% of patients obtain relief, which even then is partial at best. Particularly useful treatments have been: certain antidepressants (tricyclic antidepressant [amitriptyline, nortriptyline and desipramine], serotonin-norepinephrine reuptake inhibitors [duloxetine, venlafaxine, milnacipran] and bupropion); anticonvulsants (pregabalin, gabapentin, carbamazepine and oxcarbzepine, but not lamotrigine); botulinum toxin type A (BTX-A, also called Botox®); cannabis and cannabinoid receptor agonists; dietary supplements such as injected alpha lipoic acid and lipid-soluble benfotaimine; experimental implants; deep brain stimulation, though its complications increase with time; motor cortex stimulation at a level that is no more than tingling; spinal cord stimulators and implanted spinal pumps (e.g., intrathecal pumps with opions and optionally adjunct medication such as a local anesthetic, clonidine or ziconotide, however there are significant side effects; agonists for N-methyl-D-aspartate (NMDA) such as ketamine, dextromethorphan, and memantine, though they suffer from short half-lives, weak activity or unacceptable side effects; opioids such as methadone, ketobemidone, but they have contradictory effects on NMDA; and topical (optionally transdermal) agents such as lidocaine and capsaicin, though benefits are modest and agents such as capsaicin can in fact induce pain. Hence to date treatments for neuropathic pain have been limited in efficacy, while also having substantial side effects.

Therefore there is an ongoing need for compositions that are capable of treating neuropathic pain in a safe and effective manner.

BRIEF DESCRIPTION OF THE INVENTION

The present invention provides a composition in which a surprising synergistic combination of compounds alleviates pain. In particular embodiments the pain has a neuropathic source; in other embodiments the pain is nociceptive.

In one embodiment the invention provides a pharmaceutical composition for use against pain, comprising:
   a) a sulfur-containing amino acid selected from the group consisting of: L-methionine; L-homocysteine; L-cystathionine; L-cysteine; L-cysteine sulfinic acid; hypotaurine; taurine; and their respective lower alkyl esters; and pharmaceutically acceptable salts of these sulfur-containing amino acids and their respective lower alkyl esters;
   b) a carnitine compound selected from the group consisting of: L-carnitine; lower alkyl esters of L-carnitine; and pharmaceutically acceptable salts of these carnitine compounds and their respective lower alkyl esters; and
   c) at least one citrulline compound or beta-alanine compound, wherein the compound is selected from the group consisting of: L-citrulline; lower alkyl esters of L-citrulline; beta-alanine; lower alkyl esters of beta-alanine; and pharmaceutically acceptable salts of the same.

In another embodiment the invention provides a method for treating neuropathic pain comprising providing to a patient in need thereof a pharmaceutically effective amount of a composition that comprises:
   a) a sulfur-containing amino acid selected from the group consisting of: L-methionine; L-homocysteine; L-cystathionine; L-cysteine; L-cysteine sulfinic acid; hypotaurine; taurine; and their respective lower alkyl esters; and pharmaceutically acceptable salts of these sulfur-containing amino acids and their respective lower alkyl esters;
   b) a carnitine compound selected from the group consisting of: L-carnitine; lower alkyl esters of L-carnitine; and pharmaceutically acceptable salts of these carnitine compounds and their respective lower alkyl esters; and
   c) at least one citrulline compound or beta-alanine compound, wherein the compound is selected from the group consisting of: L-citrulline; lower alkyl esters of L-citrulline; beta-alanine; lower alkyl esters of beta-alanine; and pharmaceutically acceptable salts of the same.

DETAILED DESCRIPTION OF THE INVENTION

Definitions

The invention may be better understood by reference to the following definitions for the terms as used herein.

The term "pharmaceutical composition" means a composition intended for use by medical prescription or for use as an over-the-counter drug.

The term "pain" has its usual and ordinary meaning in the medical arts, and contemplates acute as well as chronic pain, and particularly includes but is not limited to nociceptive pain, neuropathic pain, so-called phantom pain, and incident pain, among others.

The term "method for treating pain" means a therapeutic method for the alleviation of pain.

The term "patient in need thereof", as used herein with respect to compositions and methods for treating pain, means a patient who has current pain and or is medically expected to have particular future pain.

The term "patient" as used herein contemplates both human patients for medical treatment and animal patients for veterinary treatment.

The term "sulfur-containing amino acid" means an amino acid in which a sulfur atom is covalently bonded within the amino acid. Particular examples include sulfur-containing amino acids that are generated by the biosynthetic sequence that produces taurine in the human body, and include L-methionine, L-homocysteine, L-cystathionine, L-cysteine, L-cysteine sulfinic acid, hypotaurine and taurine, and pharmaceutically acceptable salts of any of the foregoing. Taurine is a particularly preferred embodiment, but the invention is not so limited. The terms L-methionine, L-homocysteine, L-cystathionine, L-cysteine, L-cysteine sulfinic acid, hypotaurine and taurine have their usual and ordinary meaning in the fields of chemistry and biochemistry.

The term "lower alkyl group" as used herein means a $C_1$-$C_5$ hydrocarbon moiety, which moiety may be linear, branched, cyclic, saturated or unsaturated.

The term "lower alkyl ester" corresponds to a compound having formula $R^1$—O—C(=O)—$R^2$ in which: one of $R^1$ and $R^2$ is a $C_1$-$C_5$ hydrocarbon moiety, which moiety may be linear, branched, cyclic, saturated or unsaturated; and the other of $R^1$ and $R^2$ is a carnitine compound, a L-citrulline compound or a beta-alanine compound. For lower alkyl esters of carnitine compounds, the carnitine compound and its alcohol correspond to the structural unit for $R^1$—O—. For lower alkyl esters of either L-citrulline compounds, beta-alanine compounds, and lipoic acids, each respective compound and its carbonyl group correspond to the structural unit for —C(=O)—$R^2$.

The term "carnitine compound" means a compound from the group consisting of L-carnitine, its lower alkyl esters, and pharmaceutically acceptable salts of L-carnitine and of its lower alkyl esters. The term "lower alkyl ester" as used herein with respect to a carnitine compound means a compound having formula $(CH_3)_3N^+$—$CH_2$—CH(—O—C(=O)—R)$CH_2$—$CO_2^-$ in which —O—C(=O)—R is a lower alkyl ester. Non-limiting examples of carnitine compounds include L-carnitine, acetyl-L-carnitine, propionyl-L-carnitine, isovaleryl-carnitine, lower alkyl esters of L-carnitine, and pharmaceutically acceptable salts of any of the foregoing. A particularly useful lower alkyl ester for purposes of the invention is acetyl-L-carnitine, but the invention is not so limited. The names of compounds in this paragraph have their usual and ordinary meaning in chemistry and biochemistry.

The term "L-citrulline compound" means a compound selected from the group consisting of L-citrulline, lower alkyl esters of L-citrulline, pharmaceutically acceptable salts of L-citrulline, and pharmaceutically acceptable salts of lower alkyl esters of L-citrulline. A particularly preferred L-citrulline compound is L-citrulline itself, but the invention is not so limited. By lower alkyl esters of L-citrulline is meant, compounds that, when in a nonionic state, have the formula $H_2N$—C(=O)—$NH_2$—$(CH_2)_3$—CH($NH_2$)—C(=O)—O—R in which R is a lower alkyl group.

The term "beta-alanine compound" means a compound selected from the group consisting of beta-alanine, lower alkyl esters of beta-alanine, pharmaceutically acceptable salts of beta-alanine, and pharmaceutically acceptable salts of lower alkyl esters of beta-alanine. A particularly preferred beta-alanine compound is beta-alanine itself, but the invention is not so limited. By lower alkyl esters of beta-alanine is meant, compounds that, when in a nonionic state, have the formula $H_2N$—$(CH_2)_2$—$C(=O)$—$O$—$R$ in which R is a lower alkyl group.

The term "lipoic acid compound" means a compound selected from the group consisting of alpha-lipoic acid, lower alkyl esters of alpha-lipoic acid, pharmaceutically acceptable salts of alpha-lipoic acid, and pharmaceutically acceptable salts of lower alkyl esters of alpha-lipoic acid. A particularly preferred lipoic acid compound is alpha-lipoic acid itself, but the invention is not so limited. By lower alkyl esters of alpha-lipoic acid is meant, compounds that, when in a nonionic state, have the formula (R)-5-(1,2-Dithiolan-3-yl)-$(CH_2)_4$—$C(=O)$—$O$—$R$ in which R is a lower alkyl group.

The term "vitamin $B_1$", "vitamin $B_2$", "vitamin $B_6$" and "vitamin $B_{12}$" have their usual and ordinary meaning in the arts of chemistry, biochemistry and nutrition. The term "vitamins $B_1$, $B_2$, $B_6$ and $B_{12}$" refers collectively to those four vitamins.

Where ranges of masses are provided herein, the ranges are inclusive of their end points and all points between them. E.g., the range of 20 milligrams to 2 grams includes both 20 milligrams and 2 grams and all points between them.

The term "dose form" refers to the form in which compositions of the invention are administered. Such dose form terms contemplate but are not limited to "tablet", "powder", "capsule", "liquid", "gel" and "spray". Where a dose form is indicated, the type of dose form has its usual and ordinary meaning in the pharmaceutical arts. The term "unit dose form" means a dose form which, when administered alone or in an incremental low multiple, provides a sufficient quantity of the composition to provide at least temporary full or significant partial alleviation of the patient's pain that is being addressed. As used herein with respect to unit dose forms the term "incremental low multiple" means an integer of from 1 to 6, such as that number of tablets.

The term "pharmaceutically acceptable" means that which is useful in preparing a pharmaceutical composition that is generally safe, non-toxic and neither biologically nor otherwise undesirable and includes that which is acceptable for veterinary use as well as human pharmaceutical use. The term "pharmaceutically acceptable salts" means salts that are pharmaceutically acceptable, as defined above, and that possess the desired pharmacological activity. In particular, the term "pharmaceutically acceptable salt" means an acid or base salt of an ingredient used in the invention, where the salt of that ingredient is of sufficient purity and quality for use in a medicament and tolerated and sufficiently non-toxic to be used in a pharmaceutical preparation.

The term "therapeutically effective amount" refers to an amount sufficient to elicit the desired biological response. The therapeutically effective amount or dose will depend on the age, sex and weight of the patient, and the current medical condition of the patient. The skilled artisan will be able to determine appropriate dosages depending on these and other factors in addition to the present disclosure.

The terms "nerve", "neuropathy" and "neuropathic pain" have their usual and ordinary meaning in the medical arts.

The following terms for nerves and neuropathy have their usual and ordinary meaning in the medical arts: "peripheral nervous system"; "cranial nerves"; "auditory nerve"; "optic nerve"; "giant axonal neuropathy"; "autonomic nerves"; "sensory nerves"; "motor nerves"; and "autosomal dominant familial amyloid neuropathy".

The following terms for neuropathic disorders have their usual and ordinary meaning in the medical arts: "diabetic neuropathy"; "hereditary neuropathy with liability to pressure palsy"; "neuropathy target esterase"; "neuropathy, ataxia, and retinitis pigmentosa" (NARP); "delayed neuropathy induced by organophosphate poisoning"; and "polyneuropathy".

The following phrases concerning causation of pain use component terms in their usual and ordinary meaning in the medical arts: "aberrant regeneration after formation of a lesion at a peripheral nerve"; "hyper-sensitized spinothalamic tract due to ongoing spontaneous activity in the peripheral system"; "central nerve pain arising from the spinothalamic tract (STT, from the spinal cord dorsal horn neurons) representing the major ascending nociceptive pathway"; "central neural hypersensitization following peripheral nerve damage"; "loss of afferent inhibition due to a drop in input of large fiber lowering interneuron activity inhibiting nociceptive neurons"; "loss of afferent inhibition due to reduced activity of the descending antinociceptive systems or loss of descending inhibition"; "deafferentation hyper-sensitivity"; "central neuron hypersensitivity due to release of proinflammatory cytokines and glutamate by glial cells induced by peripheral nerves"; and "alteration of gene expression or expression of ion channels, causing changes in neurotransmitters and response to neural input".

The following terms for compositions and treatments are used in their usual and ordinary meaning in the medical arts: "amitriptyline"; "nortriptyline"; "desipramine"; "duloxetine"; "venlafaxine"; "milnacipran"; "bupropion"; "pregabalin"; "gabapentin"; "carbamazepine"; "oxcarbzepine"; "botulinum toxin type A"; "cannabis"; "cannabinoid receptor agonists"; "alpha-lipoic acid"; "lipid-soluble benfotaimine"; "neurological-stimulating implant"; "deep brain stimulation"; "motor cortex stimulation"; "spinal cord stimulators"; "local anesthetic"; "clonidine"; "ziconotide"; "ketamine"; "dextromethorphan"; "memantine"; "methadone"; "ketobemidone"; "lidocaine"; and "capsaicin".

When the singular forms "a," "an" and "the" or like terms are used herein, they will be understood to include plural referents unless the context clearly dictates otherwise. Thus, for example, reference to "a hydrocarbon" includes mixtures of two or more such hydrocarbons, and the like. The word "or" or like terms as used herein means any one member of a particular list and also includes any combination of members of that list.

When used herein the term "about" or "ca." will compensate for variability allowed for in the pharmaceutical industry and inherent in pharmaceutical products, such as differences in product strength and bioavailability due to manufacturing variations and time-induced product degradation. The term allows for any variation which in the practice of pharmaceuticals would allow the product being evaluated to be considered pharmaceutically equivalent or bioequivalent, or both if the context requires, to the recited strength of a claimed product. It will be understood that all numeric values expressed in this document can be prefaced by the term "about."

Technical Description

I have discovered that surprisingly certain compounds that do not individually alleviate pain to a substantial degree have a synergistic pain-relieving action when used in combination. In particular, taurine, L-carnitine, together with L-citrulline and or beta-alanine provide particular benefits. These are further enhanced when combined with alpha-lipoic acid and or certain B vitamins.

Either taurine or L-carnitine may be derived by supplements containing intermediates found in their respective human biosynthetic pathways. Similarly the action of native esterases on low alkyl esters of either taurine or L-carnitine provides respective access to these compounds. And pharmaceutically acceptable salts of any of these compounds are useful according to the invention.

The compounds include species of the taurine class.

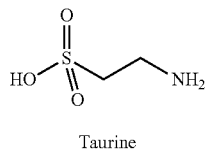

Taurine

By taurine class is meant, sulfur-containing amino acids that are part of the biosynthetic sequence that generates taurine in the human body, and their esters, and pharmaceutically acceptable salts of these amino acids and their esters. These amino acids include particularly L-methionine, L-homocysteine, L-cystathionine, L-cysteine, L-cysteine sulfinic acid, hypotaurine, and taurine. Taurine in particular is useful for this purpose, but the invention is not so limited.

An additional category of compounds used in the invention is species of the carnitine class.

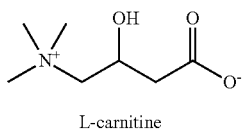

L-carnitine

By carnitine class is meant, L-carnitine and its lower alkyl esters and pharmaceutically acceptable salts of L-carnitine and of those esters, and they include but are not limited to L-carnitine, acetyl-carnitine, propionyl-carnitine, isovaleryl-carnitine, other lower alkyl esters of L-carnitine, and pharmaceutically acceptable salts of any of the foregoing. By lower alkyl is meant here and elsewhere in this description groups containing a moiety R in which R is a $C_1$-$C_5$ hydrocarbon moiety, which moiety may be linear, branched, cyclic, saturated or unsaturated. A particularly useful member of this class for purposes of the invention is acetyl-carnitine, but the invention is not so limited.

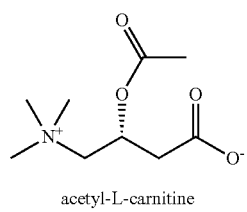

acetyl-L-carnitine

A third category of compounds used in the invention is species of the citrulline class.

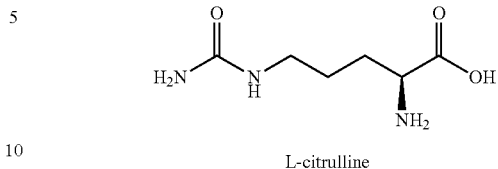

L-citrulline

By citrulline class is meant, L-citrulline and lower alkyl esters and pharmaceutically acceptable salts of L-citrulline, and they include but are not limited to L-citrulline, lower alkyl esters of L-citrulline, and pharmaceutically acceptable salts of any of the foregoing. A particularly useful member of this class for purposes of the invention is L-citrulline, but the invention is not so limited.

A fourth category of compounds used in the invention is species of the alanine class. This class may be used in combination with or in the alternative to the citrulline class.

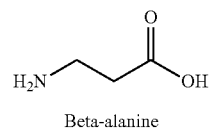

Beta-alanine

By alanine class is meant, beta-alanine and lower alkyl esters of beta alanine, and pharmaceutically acceptable salts of any of the foregoing. A particularly useful member of this class for purposes of the invention is beta-alanine, but the invention is not so limited.

In certain embodiments the nitrogens of the taurine compound, citrulline compound and/or beta-alanine compound are further alkylated by one or more lower alkyl groups.

Non-limiting illustrative pharmaceutically acceptable salts include acid addition salts which may, for example, be formed by reacting the drug compound with a suitable pharmaceutically acceptable acid such as hydrochloric acid, sulfuric acid, fumaric acid, acid, succinic acid, acetic acid, benzoic acid, citric acid, tartaric acid, carbonic acid or phosphoric acid. See, generally, S. M. Berge, et al., "Pharmaceutical Salts", J. Pharm. Sci., 1977, 66:1-19, and Handbook of Pharmaceutical Salts, Properties, Selection, and Use, 2002, Stahl and Wermuth, Eds., Wiley-VCH and VHCA, Zurich. Preferred pharmaceutically acceptable salts are those that are pharmacologically effective and suitable for contact with the tissues of patients without undue toxicity, irritation, or allergic response. A compound may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosultates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates. In some embodiments a combination or mixture of pharmaceutically acceptable anions is used. In certain embodiments the salt is a salt of an ammonium compound, for instance an acid addition salt of an amine on taurine or L-citrulline or beta-alanine, or is the quaternary ammonium salt on L-carnitine.

Additionally and or alternatively pharmaceutically acceptable salts include base addition salts, for instance carboxylate and sulfonate salts. The counterion is a pharmaceutically acceptable cation selected from among the inorganic cations such as, e.g., $Na^+$, $K^+$, $Li^+$, $Mg^{2+}$, $Ca^{2+}$, and $Zn^{2+}$, and or selected from among the organic cations such as the sugar amines, alkaloids, amino acid peptides, nucleotides, nucleic acids, small molecule amines having low toxicity, and antibiotics containing a basic nitrogen atome. In some embodiments a combination or mixture of cations is used.

In certain embodiments the composition is a dose form in the form of a tablet, a powder, a capsule, a liquid, a gel or a spray. Oral dosage forms will generally include an inert diluent or an edible carrier. They may be enclosed in gelatin capsules (for oral use) or compressed into tablets (for oral or buccal use) or formulated into troches (for buccal use). For these and other dose forms, the active compounds can be incorporated with excipients and used in the form of tablets, troches, or capsules. Pharmaceutically compatible binding agents, and/or adjuvant materials can be included as part of the composition.

Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, or corn starch; a lubricant such as magnesium stearate; a gliding agent such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain other materials for physical modification of the dose unit, e.g., coatings of sugar, shellac, or other enteric agents.

In particular embodiments a single dose comprises two to four tablets provided at least one hour before a meal, however the invention is not so limited. In various embodiments each class of compounds taught herein is represented in the composition in an amount independently selected from the range of: 1 milligram (mg) to 2 grams (g); 2 mg to 1.8 g; 5 mg to 1.6 g; 10 mg to 1.4 g; 15 mg to 1.2 g; 20 mg to 1.0 g; 25 mg to 800 mg; 30 mg to 600 mg; 35 mg to 400 mg; 40 mg to 200 mg; or 50 mg to 100 mg. In a certain embodiment a single dose is in the form of two tablets, wherein in each table the sulfur-containing amino acid is present in an amount selected from the range of 20 milligrams to 2 grams; the carnitine compound is present in an amount selected from the range of 20 milligrams to 2 grams; the citrulline compound if present is present in an amount selected from the range of 10 milligrams to 1 gram, and the beta-alanine compound if present is present in an amount selected from the range of 5 milligrams to 500 milligrams. In a particular embodiment a single dose is in the form of two tablets, wherein in each tablet the sulfur-containing amino acid is present in an amount of 200 milligrams; the carnitine compound is present in an amount of 200 milligrams; the citrulline compound is present is present in an amount of 100, and the beta-alanine compound is present in an amount of 50 milligrams.

In certain embodiments the composition further comprises at least one of vitamins $B_1$, $B_2$, $B_6$ and $B_{12}$. In some embodiments the amount of any of $B_1$, $B_2$, and $B_6$, if included in a unit dose form, is selected from one of the following ranges: 0.05 milligram (mg) to 100 mg; 0.10 mg to 90 mg; 0.25 mg to 80 mg; 0.50 mg to 70 mg; 0.75 mg to 60 mg; 1 mg to 50 mg; 1.25 mg to 40 mg; 1.5 mg to 30 mg; 1 mg to 20 mg; 2.0 mg to 10 mg; and 2.5 mg to 5.0 mg. In some embodiments the amount of $B_{12}$, if included in a unit dose form, is selected from one of the following ranges: 0.30 microgram (mcg) to 625 mcg; 0.60 mcg to 562 mg; 1.5 mcg to 500 mcg; 3.0 mcg to 437 mcg; 4.5 mcg to 375 mcg; 6.0 mcg to 312 mcg; 7.5 mcg to 250 mcg; 9.0 mcg to 187 mcg; 6.0 mcg to 125 mcg; 12 mcg to 62 mcg; and 15 mcg to 31 mcg. Alternatively, a therapeutically effective amount of vitamin B12 can range from 500, 600, 700, 800 or 900 mcg to 5,000, 4,000, 3,000, 2,000, or 1,500 mcg of vitamin B12 per day; if high ranges are desired they are preferably from 500 to 2,00 mcg, or from 800 to 1,200 mcg, and most preferably 1,000 mcg per day. Any of these vitamin B12 doses can be administered once as a single dose, or divided into two, three or four doses, per day.

In various embodiments the composition further comprises a lipoic acid selected from the group consisting of alpha-lipoic acid, lower alkyl esters of alpha lipoic acid, and pharmaceutically acceptable salts of the foregoing. In some embodiments the lipoic acid is alpha-lipoic acid. In some embodiments the amount of lipoic acid, if included in a unit dose form, is selected from one of the following ranges: 1 milligram (mg) to 2 grams (g); 2 mg to 1.8 g; 5 mg to 1.6 g; 10 mg to 1.4 g; 15 mg to 1.2 g; 20 mg to 1.0 g; 25 mg to 800 mg; 30 mg to 600 mg; 35 mg to 400 mg; 40 mg to 200 mg; and 50 mg to 100 mg.

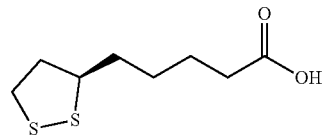

alpha-lipoic acid

In some embodiments the pain treated is neuropathic pain associated with a nerve selected from the group consisting of the peripheral nervous system, cranial nerves, auditory nerve, optic nerve, giant axonal neuropathy, autonomic nerves, sensory nerves, motor nerves, an autosomal dominant familial amyloid neuropathy.

In some embodiments the pain treated is neuropathic pain associated with a disorder selected from the group consisting of diabetic neuropathy, hereditary neuropathy with liability to pressure palsy, neuropathy target esterase, "neuropathy, ataxia, and retinitis pigmentosa" (NARP), delayed neuropathy induced by organophosphate poisoning, and polyneuropathy.

In some embodiments the pain treated is neuropathic pain diagnosed as arising from a cause selected from one of the following: aberrant regeneration after formation of a lesion at a peripheral nerve; and hyper-sensitized spinothalamic tract due to ongoing spontaneous activity in the peripheral system. By contrast, central nerve pain arises from the spinothalamic tract (STT, from the spinal cord dorsal horn neurons) representing the major ascending nociceptive pathway; central neural hypersensitization following peripheral nerve damage; loss of afferent inhibition due to a drop in input of large fiber lowering interneuron activity inhibiting nociceptive neurons; loss of afferent inhibition due to reduced activity of the descending antinociceptive systems or loss of descending inhibition; deafferentation hypersensitivity; central neuron hypersensitivity due to release of proinflammatory cytokines and glutamate by glial cells induced by peripheral nerves; and alteration of gene expression or expression of ion channels, causing changes in neurotransmitters and response to neural input.

In some embodiments the pain treated is neuropathic pain that has not responded to treatment by at least one of the following: amitriptyline; nortriptyline; desipramine; duloxetine; venlafaxine; milnacipran; bupropion; pregabalin; gabapentin; carbamazepine; oxcarbzepine; botulinum toxin type A; cannabis; other cannabinoid receptor agonists; alpha-lipoic acid; lipid-soluble benfotaimine; a neurological-stimulating implant; deep brain stimulation; motor cortex stimulation; spinal cord stimulators; a local anesthetic; clonidine; ziconotide; ketamine; dextromethorphan; memantine; methadone; ketobemidone; lidocaine; and capsaicin.

Examples of Compositions

The following TABLE 1 provides non-limiting illustrative embodiments of compositions of the invention. In a particularly preferred embodiment the unit dose is in the form of one or two tablets or one or two capsules, however the unit dose may alternatively be a powder, a liquid, a gel, or a spray. In particular embodiments these compositions are used to mitigate pain in a patient suffering from a form of pain described above in earlier sections.

TABLE 1: ILLUSTRATIVE COMPOSITIONS

| | Component | | | | |
|---|---|---|---|---|---|
| Ex. No. | S-Containing Amino Acid(s) and unit dose | Carnitine Compound and unit dose | Citrulline and/or Beta-Alanine Compound and unit dose(s) | B Vitamin and unit dose(s) | Lipoic Acid and unit dose |
| 1 | Taurine 200 mg | Acetyl-L-Carnitine 200 mg | L-Citrulline 100 mg Beta-Alanine 50 mg | — | — |
| 2 | Taurine 200 mg | Acetyl-L-Carnitine 200 mg | L-Citrulline 100 mg Beta-Alanine 50 mg | $B_{12}$ 20 mcg | Alpha-Lipoic Acid 80 mg |
| 3 | Taurine 200 mg | Acetyl-L-Carnitine 200 mg | L-Citrulline 100 mg Beta-Alanine 50 mg | $B_1$ 4 mcg $B_2$ 4 mcg $B_6$ 4 mcg $B_{12}$ 20 mcg | Alpha-Lipoic Acid 60 mg |
| 4 | Taurine 100 mg | Acetyl-L-Carnitine 400 mg | L-Citrulline 25 mg Beta-Alanine 75 mg | — | Alpha-Lipoic Acid 100 mg |
| 5 | Taurine 400 mg | Propionyl-L-Carnitine 50 mg | L-Citrulline 10 mg | $B_{12}$ 10 mcg | — |
| 6 | Taurine, Sodium salt 50 mg | Valeryl-L-Carnitine 200 mg | Beta-Alanine 50 mg | $B_{12}$ 5 mcg | Alpha-Lipoic Acid 10 mg |
| 7 | Taurine*HCl 250 mg | L-Carnitine 150 mg | L-Citrulline*HCl 100 mg Beta-Alanine*HCl 50 mg | $B_{12}$ 15 mcg | Alpha-Lipoic Acid 8 mg |
| 8 | Hypotaurine 175 mg | L-Carnitine, NaHSO$_4$, salt 150 mg | L-Citrulline*HCl 100 mg Beta-Alanine*HCl 50 mg | $B_1$ 2.5 mg | Methyl Alpha-Lipoate 1 mg |
| 9 | Hypotaurine, Magnesium salt 15 mg | Butyryl-L-carnitine*NaHSO$_4$ 150 mg | L-Citrulline (methyl ester) 100 mg | $B_2$ 4 mg | Ethyl Alpha-Lipoate 200 mg |
| 10 | Hypotaurine, Phosphoric acid salt 40 mg | L-Carnitine* Mono-potassium Citrate 50 mg | Beta-Alanine (cyclobutyl ester) 50 mg | $B_6$ 1 mg | Calcium Alpha-Lipoate 40 mg |
| 11 | Hypotaurine 5 mg | L-Carnitine* Malic acid salt 500 mg | Beta-Alanine*HCl 25 mg | — | — |
| 12 | Hypotaurine 500 mg | L-Carnitine* Bis-sodium Phosphate 25 mg | L-Citrulline, lithium salt 10 mg Beat-Alanine 90 mg | $B_1$ 1 mg $B_{12}$ 1 mcg | Manganese Alpha-Lipoate, 1 mg |
| 13 | L-methionine 20 mg | L-Carnitine 40 mg | Beta-Alanine, Fumaric Acid Salt 200 mg | $B_2$ 5 mg $B_6$ 10 mg | Alpha-Lipoic Acid, 150 mg |
| 14 | L-methionine 80 mg | L-Carnitine*Malic Acid Salt 65 mg | L-Citrulline 30 mg | $B_1$ 5 mg $B_6$ 10 mg | Alpha-Lipoic Acid 15 mg |
| 15 | L-methionine*Tartaric Acid Salt 350 mg | Butyrl L-Carnitine 135 mg | L-Citrulline, Zinc Salt 10 mg Beta-Alanine, Potassium Salt 90 mg | $B_1$ 0.3 mg $B_2$ 0.4 mg | Alpha-Lipoic Acid, Glucosamine Salt 350 mg |
| 16 | O-Methyl-L-methionine*HCl 0.2 mg | Methyl-L-Carnitine 40 mg | Beta-Alanine, Maleic Acid Salt 200 mg | $B_1$ 50 mcg $B_{12}$ 0.05 mcg | Sec-Butyl Alpha-Lipoate 35 mg |
| 17 | L-Methionine, Galactosamine Salt 8 mg | i-Propyl-L-Carnitine 6 mg | L-Citrulline 3 mg | $B_{12}$ 10 mg | Alpha-Lipoic Acid 1.5 mg |

TABLE 1: ILLUSTRATIVE COMPOSITIONS-continued

| | Component | | | | |
|---|---|---|---|---|---|
| Ex. No. | S-Containing Amino Acid(s) and unit dose | Carnitine Compound and unit dose | Citrulline and/or Beta-Alanine Compound and unit dose(s) | B Vitamin and unit dose(s) | Lipoic Acid and unit dose |
| 18 | L-Homocysteine 50 mg | Ethyl L-Carnitine 50 mg | L-Citrulline 25 mg Beta-Alanine 12 mg | — | — |
| 19 | L-Homocysteine 75 mg | Ethyl L-Carnitine 5 mg | L-Citrulline, Fructosamine Salt 50 mg O-Methyl-Beta-Alanine 10 mg | $B_2$ 50 mg | 2-Pentyl Alpha-Lipoate 5 mg |
| 20 | O-Ethyl-L-Homocysteine 2 mg | t-Butyl-L-Carnitine 5 mg | L-Citrulline, Calcium Salt 5 mg | $B_6$ 1.5 mg | Alpha-Lipoate, L-Histidine Salt 2 mg |
| 21 | L-Homocysteine, Lactic Acid Salt 1.2 mg | L-Carnitine, Benzoic Acid Salt 2.5 mg | Beta-Alanine, Mannosamine Salt 1 mg | — | Alpha-Lipoate, L-Histidine Salt 0.5 mg |
| 22 | O-n-Butyl-L-Homocysteine, Methoxybenzoic Acid Salt 125 mg | L-Carnitine, Phthalic Acid Salt 25 mg | Beta-Alanine*Sulfinic Acid Salt 10 mg | $B_{12}$ 0.2 mcg | — |
| 23 | L-Cystathionine 100 mg | L-Carnitine, 100 mg | L-Citrulline 50 mg Beta-Alanine 25 mg | — | Alpha-Lipoate Acid, 40 mg |
| 24 | L-Cystathionine, Glucamine Salt 25 mg | Sec-Butyl-L-Carnitine, 25 mg | L-Citrulline, Potassium Bicarbonate Salt 12 mg | $B_1$ 10 mg $B_2$ 10 mg | Alpha-Lipoate Acid, 20 mg |
| 25 | Isovaleryl-L-Cystathionine 0.75 mg | Sec-Butyl-L-Carnitine, Bisulfite Salt 1.5 mg | Beta-Alanine 0.5 mg | — | — |
| 26 | Methyl-L-Cystathionine, Dinitrobenzoate Salt 7.5 mg | L-Carnitine, Phenylpropionate Salt 20 mg | Beta-Alanine, Phenylacetate Salt 6 mg | $B_6$ 1 mg $B_{12}$ 10 mg | Zinc Alpha-Lipoate, 5 mg |
| 27 | L-Cystathionine, 75 mg | L-Carnitine, Sulfonate Salt 200 mg | L-Citrulline, Hydrobenzoate Salt 60 mg | $B_2$ 1 mg $B_6$ 0.5 mg $B_{12}$ 20 mcg | 3-Pentyl Alpha-Lipoate 50 mg |
| 28 | L-Cysteine, 300 mg | L-Carnitine 300 mg | L-Citrulline 150 mg Beta-Alanine 75 mg | $B_{12}$ 30 mcg | Alpha-Lipoate Acid 120 mg |
| 29 | L-Cysteine, Daunosamine Salt 30 mg | L-Carnitine, Potassium Salt 15 mg | L-Citrulline 15 mg Beta-Alanine 5 mg | — | Alpha-Lipoate Acid 12 mg |
| 30 | L-Cysteine, Bisulfite Salt 70 mg | L-Carnitine, Monohydrogen Phosphate Salt 70 mg | L-Citrulline, Vanillin Salt 35 mg | $B_1$ 0.7 mg | Alpha-Lipoate Acid, Isovanillin Salt 70 mg |
| 31 | O-Ethyl-L-Cysteine, 100 mg | Phenyl-L-Carnitine 150 mg | O-n-Propyl-Beta-Alanine 40 mg | $B_2$ 7 mg | 3-Pentyl-Alpha-Lipoic Acid 60 mg |
| 32 | i-Propyl-L-Cysteine, Tartrate Salt, 50 mg | L-Carnitine, Propanesulfonate Salt 80 mg | Beta-Alanine, Mandelate Salt 15 mg | $B_6$ 0.1 mg | — |
| 33 | L-Cysteine Sulfinic Acid 30 mg | L-Carnitine 30 mg | L-Citrulline 15 mg Beta-Alanine 7 mg | $B_{12}$ 3 mcg | Alpha-Lipoate Acid 12 mg |
| 34 | L-Cysteine Sulfinic Acid, Acetic Acid Salt 30 mg | L-Carnitine 30 mg | L-Citrulline, Acetic Acid Salt 20 mg Beta-Alanine, Acetic Acid Salt 10 mg | — | Alpha-Lipoate Acid 12 mg |
| 35 | L-Cysteine Sulfinic Acid, 1:1 Complex with $B(OH)_3$ 50 mg | L-Carnitine, 1:1 Complex with $B(OH)_3$ 35 mg | L-Citrulline, 1:1 Complex with $B(OH)_3$ 17 mg | $B_2$ 0.6 mg | — |
| 36 | L-Cysteine, Potassium Salt, 100 mg | Phenyl-L-Carnitine, Potassium Salt 100 mg | Beta-Alanine, Potassium Salt 30 mg | $B_6$ 3.5 mg | Potassium Lipoate 10 mg |
| 37 | O-4-(2-Methyl-but-2-ene)-L-Cysteine Naphthalene Sulfonate Salt, 1 mg | L-Carnitine 5 mg | Beta-Alanine, Naphthalene Sulfonate Salt 1.5 mg | $B_2$ 3 mg $B_{12}$ 25 mcg | Alpha-Lipoate Acid 120 mg |

This description is illustrative, and the invention is not so limited. Numerous permutations, variations, derivatives and modifications of this invention as described herein will occur to persons of ordinary skill in the art. The full scope of those differences is within the scope of the invention and contemplated herein.

The invention claimed is:
1. A pharmaceutical composition consisting of:
a) a sulfur-containing amino acid selected from the group consisting of at least one of L-methionine, L-homocysteine, L-cystathionine, L-cysteine, L-cysteine sulfinic acid, hypotaurine, taurine, lower alkyl esters of the sulfur-containing amino acid, and pharmaceutically acceptable salts of the sulfur-containing amino acid;
b) a carnitine compound selected from the group consisting of L-carnitine, a lower alkyl ester of L-carnitine, and a pharmaceutically acceptable salt of L-carnitine;
c) at least one of a beta-alanine compound and a citrulline compound, wherein the beta-alanine compound is selected from the group consisting of beta-alanine, a lower alkyl ester of beta-alanine, and a pharmaceutically acceptable salt of beta-alanine, and the citrulline compound is selected from the group consisting of L-citrulline, a lower alkyl ester of L-citrulline, and a pharmaceutically acceptable salt of L-citrulline;
d) optionally at least one of vitamins selected from the group consisting of $B_1$, $B_2$, $B_6$ and $B_{12}$;
e) optionally a lipoic acid compound; and
f) optionally an excipient, a binding agent, an adjuvant, a lubricant, a gliding agent, a sweetening agent, a flavoring agent, or a liquid carrier.

2. The composition of claim 1, wherein the weight ratio of the sulfur-containing amino acid to the beta-alanine compound is from 1:1 to 7.5:1.

3. The composition of claim 1, wherein the weight ratio of the sulfur-containing amino acid to the beta-alanine compound is from 2.5:1 to 6:1.

4. The composition of claim 1, wherein the composition is a unit dose form, wherein the sulfur-containing amino acid is present in the unit dose form in an amount from 20 milligrams to 2 grams; the carnitine compound is present in the unit dose form in an amount from 20 milligrams to 2 grams; and the beta-alanine compound is present in the unit dose form in an amount from 5 milligrams to 500 milligrams.

5. The composition of claim 1, wherein the sulfur-containing amino acid is taurine in an amount of from 25 mg to 800 mg.

6. The composition of claim 1, wherein the carnitine compound is L-carnitine or the pharmaceutically acceptable salt thereof in an amount of from 25 mg to 800 mg.

7. The composition of claim 1, wherein the beta-alanine compound is beta-alanine in an amount of from 2 mg to 200 mg.

8. The composition of claim 1, wherein a beta-alanine compound and a citrulline compound are present in the composition.

9. The composition of claim 8, wherein the citrulline compound is L-citrulline in an amount of from 25 mg to 800 mg.

10. The composition of claim 1, wherein the composition consists of taurine in an amount of from 35 mg to 400 mg; L-carnitine or the pharmaceutically acceptable salt thereof in an amount of from 35 mg to 400 mg; L-citrulline in an amount of from 35 mg to 400 mg; and beta-alanine in an amount of from 2 mg to 100 mg.

11. The composition of claim 1, wherein at least one of vitamins $B_1$, $B_2$, $B_6$ and $B_{12}$ is present in the composition.

12. The composition of claim 1, wherein vitamin B12 is present in the composition in an amount of from 0.30 mcg to 625 mcg.

13. The composition of claim 1, wherein the lipoic acid compound is present in the composition, wherein the lipoic acid compound is selected from the group consisting of alpha-lipoic acid, a lower alkyl ester of alpha lipoic acid, and a pharmaceutically acceptable salt of alpha-lipoic acid.

14. The composition of claim 1, wherein the lipoic acid compound is present in the composition in an amount of from 2 mg to 1 g.

15. The composition of claim 1, wherein the composition comprises taurine in an amount of from 35 mg to 400 mg; L-carnitine or the pharmaceutically acceptable salt thereof in an amount of from 35 mg to 400 mg; L-citrulline in an amount of from 35 mg to 400 mg; and beta-alanine in an amount of from 2 mg to 100 mg; vitamin B12 in an amount of from 7.5 mcg to 250 mcg; and alpha-lipoic acid in an amount of from 2 mg to 800 mg.

16. The composition of claim 1, wherein the composition is in the form of a tablet, a powder, a capsule, a liquid, a gel or a spray.

17. A method for treating pain comprising providing to a patient in need thereof a therapeutically effective amount of the composition of claim 1.

18. The method of claim 17, wherein the pain comprises acute pain, chronic pain, nociceptive pain, or incident pain.

19. The method of claim 17, wherein the pain comprises a feeling of burning or coldness, stabbing tingling, numbness, or itching.

20. The method of claim 17, wherein the pain comprises neuropathic pain.

21. The method of claim 20, wherein the neuropathic pain is associated with a nerve selected from the group consisting of: peripheral nervous system; cranial nerves; auditory nerve; optic nerve; giant axonal neuropathy; autonomic nerves; sensory nerves; motor nerves; and autosomal dominant familial amyloid neuropathy.

22. The method of claim 20, wherein the neuropathic pain is associated with a disorder selected from the group consisting of: diabetic neuropathy; hereditary neuropathy with liability to pressure palsy; neuropathy target esterase; "neuropathy, ataxia, and retinitis pigmentosa" (NARP); delayed neuropathy induced by organophosphate poisoning; and polyneuropathy.

23. The method of claim 20, wherein the neuropathic pain arises from a cause selected from one of the following: aberrant regeneration after formation of a lesion at a peripheral nerve; hyper-sensitized spinothalamic tract due to ongoing spontaneous activity in the peripheral system; central nerve pain arising from the spinothalamic tract (STT, from the spinal cord dorsal horn neurons) representing the major ascending nociceptive pathway; central neural hypersensitization following peripheral nerve damage; loss of afferent inhibition due to a drop in input of large fiber lowering interneuron activity inhibiting nociceptive neurons; loss of afferent inhibition due to reduced activity of the descending antinociceptive systems or loss of descending inhibition; deafferentation hypersensitivity; central neuron hypersensitivity due to release of proinflammatory cytokines and glutamate by glial cells induced by peripheral nerves; and alteration of gene expression or expression of ion channels, causing changes in neurotransmitters and response to neural input.

* * * * *